(12) United States Patent
Hess et al.

(10) Patent No.: US 8,440,463 B2
(45) Date of Patent: May 14, 2013

(54) PREDICTING RENAL FAILURE IN DIABETES PATIENTS BASED ON PLACENTAL GROWTH FACTOR AND SOLUBLE FLT-1

(75) Inventors: Georg Hess, Mainz (DE); Andrea Horsch, Mannheim (DE); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/909,140

(22) Filed: Oct. 21, 2010

(65) Prior Publication Data

US 2011/0033942 A1 Feb. 10, 2011

Related U.S. Application Data

(63) Continuation of application No. PCT/EP2009/055595, filed on May 8, 2009.

(30) Foreign Application Priority Data

May 13, 2008 (EP) .................................... 08156083

(51) Int. Cl.
  *G01N 33/573* (2006.01)
(52) U.S. Cl.
  USPC .............................. 436/86; 436/501; 436/811
(58) Field of Classification Search .................... 436/86, 436/63, 65, 811, 501
  See application file for complete search history.

(56) References Cited

U.S. PATENT DOCUMENTS

| 2006/0008829 A1 | 1/2006 | Hess et al. |
| 2009/0155827 A1 | 6/2009 | Zeiher et al. |

FOREIGN PATENT DOCUMENTS

| DE | 10 2004 051 847 A1 | 4/2006 |
| EP | 1615036 A1 | 1/2006 |

OTHER PUBLICATIONS

Cohen, Allison et al. "Circulating levels of the antiangiogenic marker soluble FMS-like tyrosine kinase 1 are elevated in women with pregestational diabetes and preeclampsia." Diabetes Care (2007) 30 375-377.*

James, P. Rachael et al. "Management of hypertension before, during, and after pregnancy." Heart (2004) 90 1499-1504.*
Krauss, Thomas et al. "Prospective analysis of placenta growth factor (PIGF) concentrations in the plasma of women with normal pregnancy and pregnancies complicated by preeclampsia." Hypertension in Pregnancy (2004) 23 101-111.*
Solomon, Caren G. et al. "Preeclampsia—searching for the cause." The New England Journal of Medicine (2004) 350 641-642.*
International Search Report issued Dec. 3, 2009 in PCT Application No. PCT/EP2009/055595.
International Preliminary Report on Patentability issued Aug. 27, 2010 in PCT Application No. PCT/EP2009/055595.
Gilbert, Richard E. and Marsden, Philip A., Activated Protein C and Diabetic Nephropathy, The New England Journal of Medicine, Apr. 10, 2008, pp. 1628-1630, vol. 358, No. 15.
Heeschen, Christopher et al., Plasma Levels of the Soluble fms-like Tyrosine Kinase 1 (VEGF receptor 1) Modulate the Prognostic Impact of Placental Growth Factor in Patients Post Myocardial Infarction, Circulation, Nov. 10, 2004, p. 411, Abstract 1942, vol. 110, No. 17 Supplement.
Kim, Nan Hee et al., Vascular endothelial growth factor (VEGF) and soluble VEGF receptor FLT-1 in diabetic nephropathy, Kidney International., 2005, pp. 167-177, vol. 67.
Masuyama, Hisashi et al., Circulating angiogenic factors in preeclampsia, gestational proteinuria, and preeclampsia superimposed on chronic glomerulonephritis, American Joural of Obstetrics and Gynecology, 2006, pp. 551-556, vol. 194.
Schrijvers, Bieke F. et al., The role of vascular endothelial growth factor (VEGF) in renal pathophysiology, Kidney International, 2004, pp. 2003-2017, vol. 65.
Villar, Emmanuel et al., Incidences, Treatments, Outcomes, and Sex Effect on Survival in Patients with End-Stage Renal Disease by Diabetes Status in Australia and New Zealand (1991-2005), Diabetes Care, Dec. 2007, pp. 3070-3076, vol. 30, No. 12.
English Translation of Japanese Office Action for Corresponding Japanese Patent Application No. 2011-507937, Mailing Date: Apr. 3, 2012.

* cited by examiner

*Primary Examiner* — Yelena G Gakh
*Assistant Examiner* — Christopher A Hixson
(74) *Attorney, Agent, or Firm* — Dinsmore & Shohl LLP

(57) ABSTRACT

Disclosed is a method for predicting the risk of developing renal failure or mortality for a subject suffering from diabetes mellitus. More specifically, a method is disclosed for predicting the risk of developing renal failure for a subject suffering from diabetes mellitus, the method including the steps of determining the amounts of PLGF and sFlt-1 in a sample of a subject suffering from diabetes mellitus and comparing the amounts of PLGF and sFlt-1 determined with reference amounts of PLGF and sFlt-1, whereby the risk of developing renal failure is predicted. Also disclosed are diagnostic devices and kits for carrying out the aforementioned methods.

13 Claims, 1 Drawing Sheet

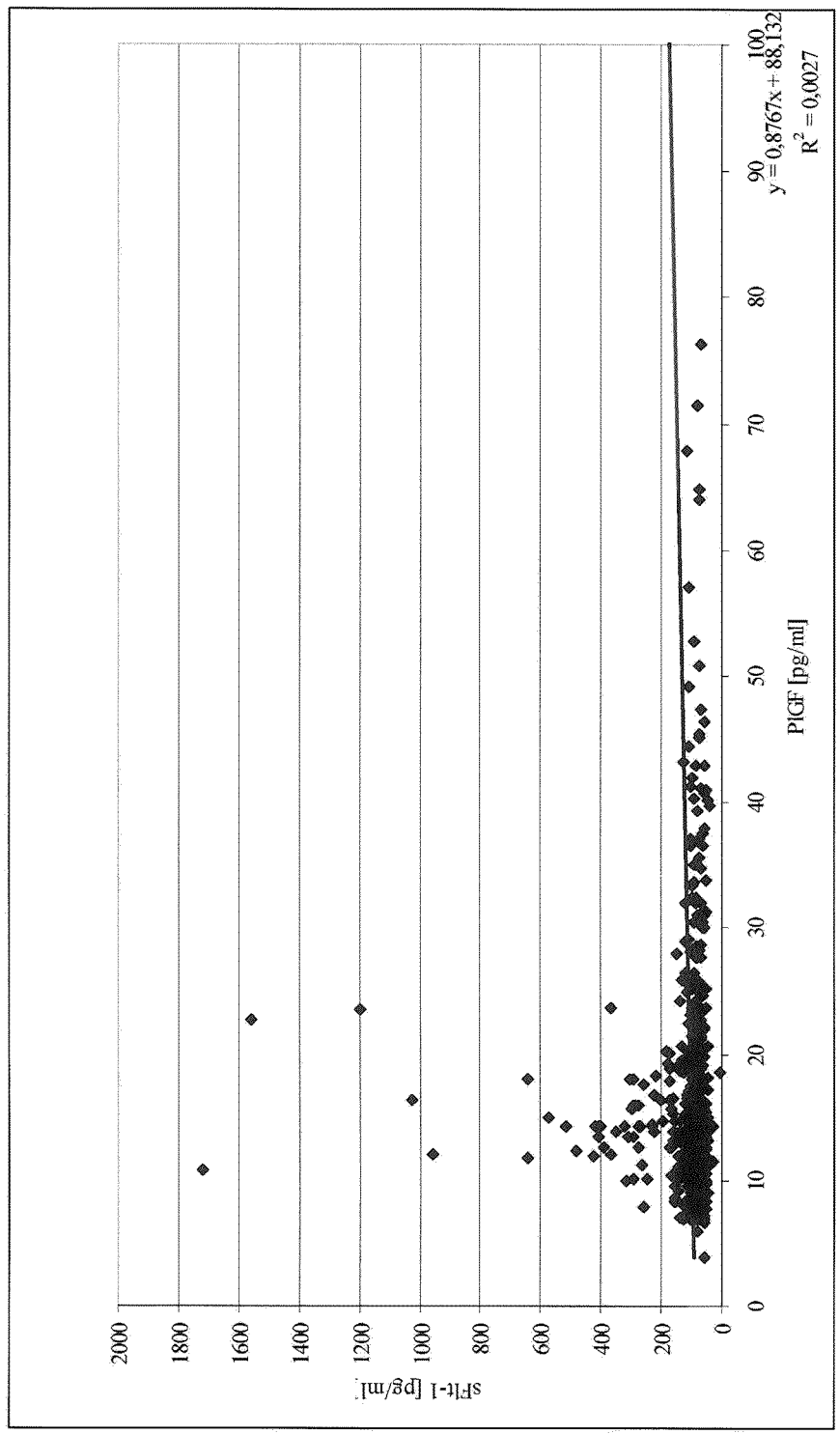

US 8,440,463 B2

PREDICTING RENAL FAILURE IN DIABETES PATIENTS BASED ON PLACENTAL GROWTH FACTOR AND SOLUBLE FLT-1

RELATED APPLICATIONS

This application is a continuation of PCT/EP2009/055595 filed May 8, 2009 and claims priority to EP 08156083.1 filed May 13, 2008.

FIELD OF THE INVENTION

The present invention relates to diagnostic means and methods. Specifically, the present invention relates to a method for predicting the risk of developing renal failure or mortality for a subject suffering from diabetes mellitus. Further, it relates to a method of diagnosing whether a subject suffering from diabetes is susceptible for a renal therapy. Finally, the present invention encompasses diagnostic devices and kits for carrying out the aforementioned methods.

BACKGROUND OF THE INVENTION

Renal failure is a major clinical complication in patients suffering from diabetes mellitus type I. Specifically, patients suffering from diabetes or being at least at risk of developing diabetes have a higher prevalence for developing renal failure than others (see, e.g., Villar 2007, Diabetes Care 30(12): 3070-3076; Gilbert 2008, N Engl J Med 358:1628-1630). Renal failure may appear as chronic or acute renal failure. While the acute form of renal failure most often can be addressed only by kidney function replacement measures such as dialysis or transplantation, the chronic form is progressing in a manner which allows for other therapeutic interventions as well. At its end stage, chronic renal failure also requires kidney function replacement measures such as dialysis or kidney transplantation. It is to be understood that these measures in light of the high costs for the health care system and the severe, inconvenient and cumbersome side effects for the patient are to be avoided. Therefore, an early intervention with the progression of renal failure is highly desirable. Suitable therapeutic measures comprise the administration of blood lowering drugs, an altered life style, and nutritional diets. A remaining issue in handling chronic renal failure, however, is its early diagnosis or an individual risk assessment for a given diabetes patient.

In EP 1 615 036 A1 angiogenesis markers have been reported in diabetes patients for assessing the risk of cardiovascular events. Specifically, the placental growth factor (PLGF), the vascular endothelial growth factor (VEGF) and soluble Flt-1 (sFlt-1) are mentioned as angiogenesis markers in general. Some of the patients also exhibited diabetic nephropathy. However, no measures for risk stratification for renal failure have been reported.

Thus, the technical problem underlying the present invention could be seen as the provision of means and methods for predicting the risk for renal failure in a subject suffering from diabetes in order to, e.g., select a suitable therapy which inhibits progression of the renal failure. The technical problem is solved y the embodiments characterized in the accompanying claims and herein below.

SUMMARY OF THE INVENTION

Accordingly, the present invention relates to a method for predicting the risk of developing renal failure for a subject suffering from diabetes mellitus comprising:

a) determining the amounts of PLGF and sFlt-1 in a sample of a subject suffering from diabetes mellitus; and
b) comparing the amounts determined in step a) with reference amounts, whereby the risk of developing renal failure is to be predicted.

The method of the present invention, preferably, is an in vitro method. Moreover, it may comprise steps in addition to those explicitly mentioned above. For example, further steps may relate to sample pre-treatments or evaluation of the results obtained by the method. The method may be carried out manually or assisted by automation. Preferably, step (a) and/or (b) may in total or in part be assisted by automation, e.g., by a suitable robotic and sensory equipment for the determination in step (a) or a computer-implemented comparison in step (b).

BRIEF DESCRIPTION OF THE FIGURE

FIG. 1: Linear regression analysis of sFlt-1 and PLGF patients suffering from diabetes type I.

DETAILED DESCRIPTION OF THE INVENTION

The term "predicting the risk" as used herein refers to assessing the probability according to which a subject will develop renal failure within a certain time window, i.e., the predictive window. In accordance with the present invention, the predictive window, preferably, is at least 2 years, at least 4 years, at least 6 years, at least 8 years, at least 10 years or at least 12 years. The predictive window, also preferably, will be the entire life span of the subject. However, as will be understood by those skilled in the art, such an assessment is usually not intended to be correct for 100% of the subjects to be diagnosed. The term, however, requires that prediction can be made for a statistically significant portion of subjects in a proper and correct manner. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the prediction of an increased, normal or decreased risk will be correct for at least 60%, at least 70%, at least 80%, or at least 90% of the subjects of a given cohort or population. The term, preferably, relates to predicting an increased risk for renal failure compared to the average risk for developing renal failure in a population of subjects suffering from diabetes.

The term "renal failure" as used herein refers to an impaired kidney function. Accordingly, during renal failure the kidney function is significantly decreased as determined by the glomerular filtration rate (GFR) or the protein content of the urine. Further symptoms of renal failure are well known in the art and described in standard text books of medicine. Preferably, a GFR of at least 60 ml/min for three or more months or detectable protein in the urine during said time period are indicative for, a chronic renal failure. More preferably, renal failure as used herein is chronic renal failure. It will be understood that severe chronic renal failure requires dialysis or transplantation of the kidney exhibiting the failure. Accordingly, the method of the present invention can be also applied to predict the need for dialysis or kidney transplantation of a patient. The term "diabetes mellitus" as used herein refers, preferably, to diabetes mellitus type I. The symptoms and clinical parameters associated with diabetes mellitus type I are well known in the art.

The term "subject" as used herein relates to animals, preferably mammals, and, more preferably, humans. However, it is envisaged by the present invention that the subject shall be suffering from diabetes mellitus as specified elsewhere herein. Except for the diabetes, the subject shall be, more preferably, apparently healthy, in particular with respect to kidney function.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein.

The term "placental growth factor (PLGF)" as used herein refers to a placenta derived growth factor which is a 149-amino-acid-long polypeptide and is highly homologous (53% identity) to the platelet-derived growth factor-like region of human vascular endothelial growth factor (VEGF). Like VEGF, PLGF has angiogenic activity in vitro and in vivo. For example, biochemical and functional characterization of PLGF derived from transfected COS-1 cells revealed that it is a glycosylated dimeric secreted protein able to stimulate endothelial cell growth in vitro (Maqlione 1993, Oncogene 8(4):925-31). Preferably, PLGF refers to human PLGF, more preferably, to human PLGF having an amino acid sequence as shown in Genebank accession number P49763, GI: 17380553 or a variant thereof. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific PLGF. Variants may be allelic variants, splice variants or any other species specific homologs, paralogs, or orthologs. Moreover, the variants referred to herein include fragments of the specific PLGF or the aforementioned types of variants as long as these fragments have the essential immunological and biological properties as referred to above. Such fragments may be, e.g., degradation products of PLGF. Further included are variants which differ due to posttranslational modifications such as phosphorylation or myristylation.

The term "soluble (s)Flt-1" as used herein refers to polypeptide which is a soluble form of the VEGF receptor Flt-1. It was identified in conditioned culture medium of human umbilical vein endothelial cells. The endogenous soluble Flt-1 (sFlt-1) receptor is chromatographically and immunologically similar to recombinant human sFlt-1 and binds [125I] VEGF with a comparable high affinity. Human sFlt-1 is shown to form a VEGF-stabilized complex with the extracellular domain of KDR/Flk-1 in vitro. Preferably, sFlt-1 refers to human sFlt-1 or a variant thereof. More preferably, human sFlt-1 can be deduced from the amino acid sequence of Flt-1 as shown in Genebank accession number P17948, GI: 125361. An amino acid sequence for mouse sFlt-1 is shown in Genebank accession number BAA24499.1, GI: 2809071. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific sFlt-1. Variants may be allelic variants, splice variants or any other species specific homologs, paralogs, or orthologs. Moreover, the variants referred to herein include fragments of the specific sFlt-1 or the aforementioned types of variants as long as these fragments have the essential immunological and biological properties as referred to above. Such fragments may be, e.g., degradation products of sFlt-1. Further included are variants which differ due to posttranslational modifications such as phosphorylation or myristylation.

Determining the amount of the polypeptides referred to in this specification relates to measuring the amount or concentration, preferably semi-quantitatively or quantitatively. Measuring can be done directly or indirectly. Direct measuring relates to measuring the amount or concentration of the polypeptide based on a signal which is obtained from the polypeptide itself and the intensity of which directly correlates with the number of molecules of the polypeptide present in the sample. Such a signal—sometimes referred to herein as intensity signal—may be obtained, e.g., by measuring an intensity value of a specific physical or chemical property of the polypeptide. Indirect measuring includes measuring of a signal obtained from a secondary component (i.e., a component not being the polypeptide itself) or a biological read out system, e.g., measurable cellular responses, ligands, labels, or enzymatic reaction products.

In accordance with the present invention, determining the amount of a polypeptide can be achieved by all known means for determining the amount of a polypeptide in a sample. Said means comprise immunoassay devices and methods which may utilize labeled molecules in various sandwich, competition, or other assay formats. Said assays will develop a signal which is indicative for the presence or absence of the polypeptide. Moreover, the signal strength can, preferably, be correlated directly or indirectly (e.g., reverse-proportional) to the amount of polypeptide present in a sample. Further suitable methods comprise measuring a physical or chemical property specific for the polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on ELECSYS analyzers, Roche Diagnostics GmbH), CBA (an enzymatic cobalt binding assay, available for example on Roche-Hitachi analyzers), and latex agglutination assays (available for example on Roche-Hitachi analyzers).

Preferably, determining the amount of a polypeptide comprises the steps of (a) contacting a cell capable of eliciting a cellular response the intensity of which is indicative of the amount of the polypeptide with the polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g., a peptide, polypeptide, or a small molecule. The expression or substance shall generate an intensity signal which correlates to the amount of the polypeptide.

Also preferably, determining the amount of a polypeptide comprises the step of measuring a specific intensity signal obtainable from the polypeptide in the sample. As described above, such a signal may be the signal intensity observed at an mass to charge (m/z) variable specific for the polypeptide observed in mass spectra or a NMR spectrum specific for the polypeptide.

Determining the amount of a polypeptide may, preferably, comprises the steps of (a) contacting the polypeptide with a specific ligand, (b) (optionally) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the polypeptide described herein. Preferred ligands include antibodies, nucleic acids, peptides or polypeptides such as receptors or binding partners for the polypeptide and fragments thereof comprising the binding domains for the peptides, and aptamers, e.g., nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g., phage display. Antibodies as referred to herein include both polyclonal and monoclonal antibodies, as well as fragments thereof, such as Fv, Fab and F(ab)2 fragments that are capable of binding, antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the polypeptide. Specific binding according to the present invention means that the ligand or agent should not bind substantially to ("cross-react" with) another peptide, polypeptide or substance present in the sample to be analyzed. Preferably, the specifically bound polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g., according to its size on a Western Blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g., by NMR or surface plasmon resonance.

Second, if the ligand also serves as a substrate of an enzymatic activity of the polypeptide of interest, an enzymatic reaction product may be measured (e.g., the amount of a protease can be measured by measuring the amount of cleaved substrate, e.g., on a Western Blot). Alternatively, the ligand may exhibit enzymatic properties itself and the "ligand/polypeptide" complex or the ligand which was bound by the polypeptide, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g., detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathione-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g., magnetic beads", including paramagnetic and superparamagnetic labels), and fluorescent labels. Enzymatically active labels include, e.g., horseradish peroxidase, alkaline phosphatase, beta-Galactosidase, Luciferase, and derivatives thereof. Suitable substrates for detection include di-amino-benzidine (DAB), 3,3'-5,5'-tetramethyl-benzidine, NBT-BCIP (4-nitro blue tetrazolium chloride and 5-bromo-4-chloro-3-indolyl-phosphate, available as ready-made stock solution from Roche Diagnostics), CDP-Star (Amersham Biosciences), ECF (Amersham Biosciences). A suitable enzyme-substrate combination may result in a colored reaction product, fluorescence or chemiluminescence, which can be measured according to methods known in the art (e.g., using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g., Alexa 568). Further fluorescent labels are available, e.g., from Molecular Probes (Oregon). Also the use of quantum dots as fluorescent labels is contemplated. Typical radioactive labels include $^{35}$S, $^{125}$I, $^{32}$P, $^{33}$P and the like. A radioactive label can be detected by any method known and appropriate, e.g.; a light-sensitive film or a phosphor imager. Suitable measurement methods according the present invention also include precipitation (particularly immunoprecipitation), electro-chemiluminescence (electro-generated chemiluminescence), RIA (radioimmunoassay), ELISA (enzyme-linked immunosorbent assay), sandwich enzyme immune tests, electro-chemiluminescence sandwich immunoassays (ECLIA), dissociation-enhanced lanthanide fluoroimmunoassay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamide gel electrophoresis (SDS-PAGE), Western Blotting, and mass spectrometry), can be used alone or in combination with labeling or other detection methods as described above.

The amount of a polypeptide may be, also preferably, determined as follows: (a) contacting a solid support comprising a ligand for the polypeptide as specified above with a sample comprising the polypeptide and (b) measuring the amount of polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g., a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "amount" as used herein encompasses the absolute amount of a polypeptide, the relative amount or concentration of the polypeptide as well as any value or parameter which correlates thereto or can be derived therefrom. Such values or parameters comprise intensity signal values from all specific physical or chemical properties obtained from the polypeptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations.

The term "comparing" as used herein encompasses comparing the amount of the polypeptide comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e., automatically provide the desired assessment in a suitable output format. Based on the comparison of the amount determined in step a) and the reference amount, it is possible to predict the risk for developing renal failure. Therefore, the reference amount is to be chosen so that either a difference or a similarity in the compared amounts allows identifying those subjects which have an increased, decreased or normal risk for developing renal failure.

Accordingly, the term "reference amounts" as used herein refers to amounts of the polypeptides which allow allocating the individual risk for developing renal failure into either the increased, decreased or normal risk group. Therefore, the reference may either be derived from (i) a subject known to have a decreased or normal risk of developing renal failure or (ii) a subject known to have an increased risk of developing renal failure. Moreover, the reference amounts, preferably, define thresholds. Suitable reference amounts or threshold amounts may be determined by the method of the present invention from a reference sample to be analyzed together, i.e., simultaneously or subsequently, with the test sample. A preferred reference amount serving as a threshold may be derived from the upper limit of normal (ULN), i.e., the upper limit of the physiological amount to be found in a population of subjects (e.g., patients enrolled for a clinical trial). The ULN for a given population of subjects can be determined by various well known techniques. A suitable technique may be to determine the median of the population for the peptide or polypeptide amounts to be determined in the method of the present invention. The ULN for PLGF referred to herein, typically, varies between 10 and 20 pg/ml. More typically, the ULN is between 12 and 15 pg/ml, most typically, it is 13 pg/ml. The ULN for sFlt-1 referred to herein, typically, varies between 80 and 150 pg/ml. More typically, the ULN for the sFlt-1 is between 90 and 120 pg/ml, most typically, it is 95 pg/ml.

In principle, it has been found that with respect to the ULN an increased amount, of PLGF and sFlt-1 are indicative for a subject suffering from diabetes and having an increased risk for developing renal failure. Thus, in a preferred embodiment of the method of the present invention, with respect to the ULN an increased amount of PLGF and sFlt-1 are indicative for said increased risk of developing renal failure.

Advantageously, it has been found in the study underlying the present invention that a combination of PLGF and sFlt-1 as biomarkers is required for predicting the risk of developing renal failure in subjects suffering from diabetes in a reliable and efficient manner. Moreover, it has been found that each of said biomarkers is statistically independent from each other. Accordingly, the method of the present invention provides for highly reliable risk stratification. Based on the individual risk, suitable therapeutic measures can be started in order to avoid the severe consequences of progressing chronic renal failure such as dialysis or transplantation. Moreover, the method of the present invention can be implemented even in portable assays, such as test strips. Therefore, the method is particularly well suited for prediction within large populations of diabetes patients even for ambulant patients. Thanks to the findings of the present invention, the severe consequences of chronic renal failure can be avoided. Moreover, it is possible to predict the need of dialysis or kidney transplantation.

The present invention also refers to a method of determining whether a subject suffering from diabetes mellitus is susceptible to a renal therapy comprising:
   a) determining the amounts of PLGF and sFlt-1 in a sample of a subject suffering from diabetes mellitus; and
   b) comparing the amounts determined in step a with reference amounts, whereby a subject susceptible to a renal therapy is to be determined.

The term "renal therapy" as used herein, preferably, relates to therapeutic measures which inhibit progression of renal failure. More preferably, said renal therapy comprises administration of blood pressure lowering drugs, most preferably, aspirin, statins, ACE inhibitors and angiotensin II receptor blockers (see Eddy 2005, Advances in Chronic Kidney Diseases 12(4):353-365). Alternatively or in addition, the term relates to life style recommendations given to a subject and/or nutritional diets, preferably, in combination with glucose level control.

The term "susceptible" as used herein means that a renal therapy applied to the subject will inhibit or at least ameliorate the progression of renal failure or its accompanying symptoms. It is to be understood that the assessment for susceptibility for the renal therapy will not be correct for all (100%) of the investigated subjects. However, it is envisaged that at least a statistically significant portion can be determined for which the renal therapy can be successfully applied. Whether a portion is statistically significant can be determined by techniques specified elsewhere herein.

In a preferred embodiment of the aforementioned method, the reference amount is the ULN. More preferably, increased amounts of PLGF and sFlt-1 with respect to the ULN are indicative for a subject susceptible to a renal therapy.

The present invention also encompasses a method for predicting the risk of mortality for a subject suffering from diabetes mellitus comprising:
   a) determining the amounts of PLGF and sFlt-1 in a sample of a subject suffering from diabetes mellitus; and
   b) comparing the amounts determined in step a) with reference amounts, whereby the risk of mortality is to be predicted.

The term "mortality" as used herein encompasses all causes of mortality. Preferably, the term relates to mortality caused by cardiovascular events.

In a preferred embodiment of the aforementioned method, the reference amount is the ULN. More preferably, increased amounts of PLGF and sFlt-1 with respect to the ULN are indicative for an increased risk of mortality.

The present invention also relates to a device for predicting the risk of developing renal failure for a subject suffering from diabetes mellitus comprising:
   a) means for determining the amount of PLGF and sFlt-1; and
   b) means for comparing the amounts determined by the means of a) with a reference amounts, whereby the device is adapted for predicting the risk of developing renal failure.

The term "device" as used herein relates to a system of means comprising at least the aforementioned means operatively linked to each other as to allow the prediction. Preferred means for determining the amount of a one of the aforementioned polypeptides as well as means for carrying out the comparison are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to obtain the desired results. Preferably, the means are comprised by a single device in such a case. Said device may accordingly include an analyzing unit for the measurement of the amount of the polypeptides in an applied sample and a computer unit for processing the resulting data for the evaluation. The computer unit, preferably, comprises a database including the stored reference amounts or values thereof recited elsewhere in this specification as well as a computer-implemented algorithm for carrying out a comparison of the determined amounts for the polypeptides with the stored reference amounts of the database. Computer-implemented as used herein refers to a computer-readable program code tangibly included into the computer unit. Alternatively, where means such as test strips are used for determining the amount of the peptides or polypeptides, the means for comparison may comprise control strips or tables allocating the determined amount to a reference amount. The test strips are, preferably, coupled to a ligand which specifically binds to the peptides or polypeptides referred to herein. The strip or device, preferably, comprises means for detection of the binding of said peptides or polypeptides to the ligand. Preferred means for detection are disclosed in connection with embodiments relating to the method of the invention above. In such a case, the means are operatively linked in that the user of the system brings together the result of the determination of the amount and the diagnostic or prognostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test strips or electronic devices which merely require loading with a sample. The results may be given as output of raw data which need interpretation by the clinician. Preferably, the output of the device is, however, processed, i.e., evaluated, raw data the interpretation of which does not require a clinician. Further preferred devices comprise the analyzing units/devices (e.g., biosensors, arrays, solid supports coupled to ligands specifically recognizing the polypeptides referred to herein, Plasmon surface resonace devices, NMR spectrometers, mass-spectrometers etc.) and/or evaluation units/devices referred to above in accordance with the method of the invention.

Furthermore, the present invention relates to a device for determining whether a subject suffering from diabetes mellitus is susceptible to a renal therapy comprising:
   a) means for determining the amount of PLGF and sFlt-1; and
   b) means for comparing the amounts determined by the means of a) with a reference amounts, whereby the device is adapted for determining whether the subject is susceptible to a renal therapy.

Even further, encompassed by this invention is a device for predicting the risk of mortality for a subject suffering from diabetes mellitus comprising:
   a) means for determining the amount of PLGF and sFlt-1; and
   b) means for comparing the amounts determined by the means of a) with a reference amounts, whereby the device is adapted for predicting the risk of mortality.

The present invention also contemplates a kit adopted for carrying out the method of the present invention comprising:
   a) means for determining the amount of PLGF and sFlt-1; and
   b) means for comparing the amounts determined by the means of a) with a reference amounts, whereby the kit is adapted for predicting the risk of developing renal failure.

The term "kit" as used herein refers to a collection of the aforementioned means, preferably, provided in separately or within a single container. The container, also preferably, comprises instructions for carrying out the method of the present invention. Preferably, the kit comprises instructions for carrying out the method of the present invention.

Moreover, encompassed by the present invention is further a kit adopted for carrying out the method of the present invention comprising:
 a) means for determining the amount of PLGF and sFlt-1; and
 b) means for comparing the amounts determined by the means of a) with a reference amounts, whereby the kit is adapted for determining whether a subject is susceptible for renal therapy.

Finally, the invention relates to a kit adopted for carrying out the method of the present invention comprising:
 a) means for determining the amount of PLGF and sFlt-1; and
 b) means for comparing the amounts determined by the means of a) with a reference amounts, whereby the kit is adapted for predicting the risk of mortality.

The following Examples shall merely illustrate the invention. They shall not be construed, whatsoever, to limit the scope of the invention.

EXAMPLE

PLGF and sFlt-1 are Predictors for an Increased Risk of Developing Renal Failure in Patients Suffering Diabetes Mellitus Type I A Total of 891 Patients Suffering from Diabetes Type I were Investigated for Blood Levels of sFlt-1 and PLGF. Blood Levels of sFlt-1 and PLGF were Determined Using the Commercially Available ELECSYS Immunoassays from Roche Diagnostics GmbH Endpoints "all cause mortality" and "renal failure" were determined after 12 years in the present outcome study.

The results of the study are summarized in the following table. Moreover, PLGF, and sFlt-1 are statistically independent from each other as shown by linear regression analysis (see FIG. 1).

TABLE

|  | all cause mortality n = 178 | ERSD n = 89 |
|---|---|---|
| PLGF (median of quartiles) | | |
| 10 pg/ml | 27 | 7 |
| 13 | 34 | 9 |
| 16 | 40 | 11 |
| 31 | 77 | 62 |
| sFlt-1 | | |
| 69 pg/ml | 32 | 19 |
| 79 | 34 | 18 |
| 95 | 37 | 15 |
| 169 | 75 | 43 |

N = 891 patients
N = 178 patients with all cause mortality
N = 89 patients with ERSD
Quartiles n = 223

What is claimed is:

1. A method for predicting a risk of developing chronic renal insufficiency in a subject suffering from diabetes mellitus type I, the method comprising:
 (a) contacting a sample from the subjects with a ligand specific for placental growth factor (PLGF);
 (b) calculating an amount of PLGF in the sample based contacting step (a);
 (c) contacting a sample from the subject with a ligand specific for soluble Flt-1 (sFlt-1);
 (d) calculating an amount of sFlt-1 in the sample based contacting of step (c)
 comparing the calculated amount of PLGF and the calculated amount of sFlt-1 with a reference amount of PLGF and a reference amount of sFlt-1, respectively; and
 predicting a risk of developing chronic renal insufficiency if the calculated amount of PLGF is greater than a reference amount of PLGF between 12 and 15 pg/ml and the calculated amount of sFlt-1 is greater than a reference amount of sFlt-1 between 90 and 120 pg/ml.

2. The method of claim 1, wherein the reference amount of PLGF is 13 pg/ml and the reference amount of sFlt-1 is 95 pg/ml.

3. A method for determining susceptibility of a subject to a renal therapy wherein the subject suffers from diabetes mellitus type I, the method comprising:
 (a) contacting a sample from the subject with a ligand specific for placental growth factor (PLGF)
 (b) calculating an amount of PLGF in the sample based on contacting step (a);
 (c) contacting a sample from the subject with a ligand specific for soluble Flt-1 (sFlt-1);
 (d) calculating an amount of sFlt-1 in the sample based on contacting step (c); and
 assessing the subject as susceptible to renal therapy if
 the calculated amount of PLGF is greater than a reference amount of PLGF between 12 and 15 pg/ml and the calculated amount of sFlt-1 is greater than a reference amount of sFlt-1 between 90 and 120 pg/ml.

4. The method of claim 3, wherein the reference amount of PLGF is 13 pg/ml and the reference amount of sFlt-1 is 95 pg/ml.

5. The method of claim 3, wherein the renal therapy is selected from the group consisting of blood pressure lowering drugs, aspirin, statins, angiotensin-converting enzyme (ACE) inhibitors, and angiotensin II receptor blockers.

6. A method for predicting a risk of mortality in a subject suffering from diabetes mellitus type I, the method comprising:
 (a) contacting a sample from the subject with a ligand specific for placental growth factor (PLGF);
 (b) calculating an amount of PLGF in the sample based on contacting step (a);
 (c) contacting a sample from the subject with a ligand specific for soluble Flt-1 (sFlt-1);
 (d) calculating an amount of sFlt-1 in the sample based on contacting step (c); and
 predicting an increased risk of mortality if the calculated amount of PLGF is greater than a reference amount of PLGF between 12 and 15 pg/ml and the calculated amount of sFlt-1 is greater than a reference amount of sFlt-1 between 90 and 120 pg/ml.

7. The method of claim 6, wherein the reference amount of PLGF is 13 pg/ml and the reference amount of sFlt-1 is 95 pg/ml.

8. The method according to claim 1 wherein the subject suffering from diabetes mellitus type I is apparently healthy with respect to kidney function.

9. The method according to claim 3 wherein the subject suffering from diabetes mellitus type I is apparently healthy with respect to kidney function.

10. The method according to claim 6 wherein the subject suffering from diabetes mellitus type I is apparently healthy with respect to kidney function.

11. The method according to claim 1 wherein predicting a risk of developing chronic renal insufficiency comprises a predictive window of at least 12 years.

12. The method according to claim 6 wherein predicting a risk of mortality comprises a predictive window of at least 12 years.

13. A method for managing treatment of a patient determining susceptibility suffering from diabetes mellitus type I, the method comprising:

determining susceptibility of the patient for a renal therapy by (a) contacting a sample from the subject with a ligand specific for placental growth factor (PLGF),
(b) calculating an amount of PLGF in the sample based on contacting step (a),
(c) contacting a sample from the subject with a ligand specific for soluble Flt-1 (sFlt-1),
(d) calculating an amount of sFlt-1 in the sample based on contacting step (c),
assessing the subject as susceptible to renal therapy if the calculated amount of PLGF is greater than a reference amount of PLGF between 12 and 15 pg/ml and the calculated amount of sFlt-1 is greater than a reference amount of sFlt-1 between 90 and 120 pg/ml; and
initiating a treatment for renal insufficiency if the patient is susceptible to renal therapy, wherein the treatment comprises administration of blood pressure lowering drugs, aspirin, statins, angiotensin-converting enzyme (ACE) inhibitors, angiotensin II receptor blockers or combinations thereof.

* * * * *